United States Patent [19]

Szonntagh

[11] 4,382,698

[45] May 10, 1983

[54] COMBUSTIBLE GAS ANALYZER

[75] Inventor: Eugene L. Szonntagh, Flourtown, Pa.

[73] Assignee: Honeywell Inc., Minneapolis, Minn.

[21] Appl. No.: 244,537

[22] Filed: Mar. 17, 1981

[51] Int. Cl.³ .............................................. G01N 25/22
[52] U.S. Cl. ................................................... 374/37
[58] Field of Search .............. 73/190 CV; 422/51, 54, 422/98; 374/36, 37

[56] References Cited

U.S. PATENT DOCUMENTS

| 3,393,562 | 7/1968 | Breedlove . | |
|---|---|---|---|
| 3,485,606 | 12/1969 | Olivier | 422/51 X |
| 4,125,123 | 11/1978 | Clingman, Jr. | 73/190 X |

FOREIGN PATENT DOCUMENTS 8151  8/1979  European Pat. Off. .

*Primary Examiner*—Herbert Goldstein
*Attorney, Agent, or Firm*—Laurence J. Marhoefer; Lockwood D. Burton; Mitchell J. Halista

[57] ABSTRACT

A combustible gas analyzer for determining the Wobbe Index of a combustible gas uses a constant pressure combustible gas supply and constant flow rate air supply to provide oxygen and gas for combustion. The air is supplied directly to be mixed with the combustible gas while the gas is passed through a variable orifice or valve before mixing with the air supply. A zirconium oxide detector is arranged to measure the oxygen content of the combustion products to enable a predetermined oxygen level to be reached. The valve is operated by a valve control response to the output of the zirconium oxide detector to maintain the preset oxygen level. The position of the valve is monitored as a representation of the Wobbe Index of the combustible gas.

10 Claims, 1 Drawing Figure

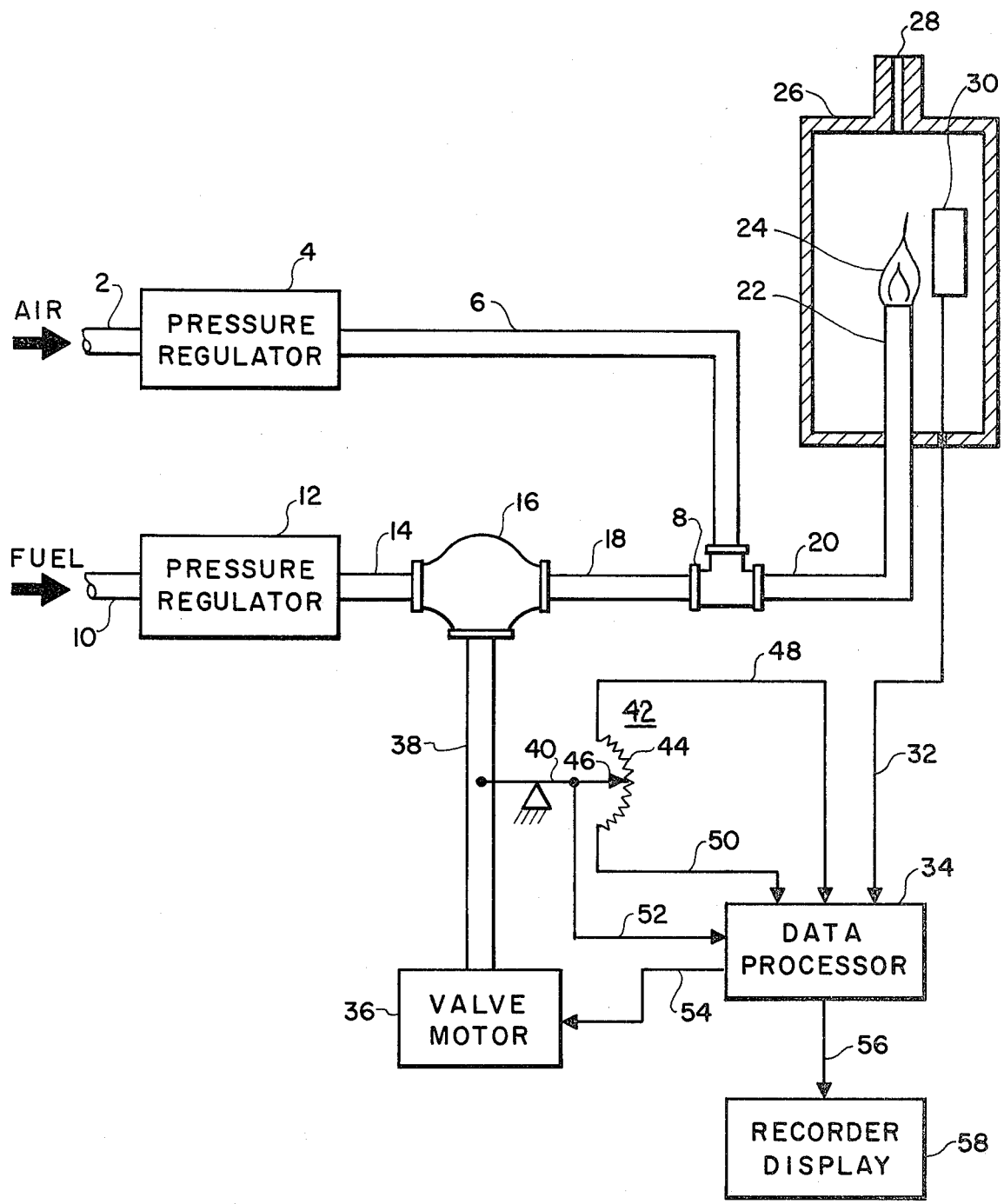

COMBUSTIBLE GAS ANALYZER

BACKGROUND OF THE INVENTION

1. Field of the Invention

The present invention is directed to combustible gas analysis apparent. More specifically, the present invention is directed to a gas analysis apparatus for determining the heating Wobbe Index of combustible gases.

2. Description of the Prior Art

The well-known Wobbe Index of a combustible gas is defined as the amount of heat released by a burner of constant orifice, McGraw-Hill Dictionary of Science, 1979 and stated mathematically by the following relation:

$W = H/\sqrt{SG}$ where H is the caloric combustion value of the gas per unit volume, e.g., BTU/ft$^3$, and SG is specific gravity of the combustible gas. The Wobbe Index is a quantity used in heating technology since different combinations of gases supplied to a gas heated apparatus under the same pressure provide equal heat production from the apparatus whereby the apparatus does not need to be readjusted as long as the Wobbe Index is maintained at a predetermined value. For example, if a mixture of gases from different sources is burned in an industrial heating operation, the gases must be mixed in such proportion so that a gas is obtained having a constant Wobbe Index. One prior art method of determining the Wobbe Index of the gas involves the combination of a caloriometer, a density meter and a computing circuit, e.g., a microprocessor. These parts while they may be combined into a single instrument produce an overall device which is very costly and exhibits a sluggish operation whereby rapid changes in the gas mixture are measured at a slow rate and the resulting correction, if necessary, is also applied at a corresponding slow rate. It has been discovered that when gas mixtures having different compositions and different Wobbe indices are burned with equal quantities of air, the oxygen content of the exhaust gas shows a direct correlation with the Wobbe Index. Accordingly, for purposes of measurement and control, it is not necessary to measure the Wobbe Index as such and it is sufficient to measure only the oxygen content in the exhaust gas. One prior art apparatus for producing this type of operation includes a sampling line containing a flow control nozzle for withdrawing a gas sample, a means for adjusting the gas sample so that the pressure difference through this control nozzle has an adjustable constant value, a means for feeding a constant volume of air as a source of combustion oxygen into the gas stream sample, a combustion chamber, a burner in the combustion chamber to completely burn the gas-air mixture, an outlet for the burned gas from the combustion chamber and an oxygen sensor in the combustion chamber to sense the oxygen content of the exhaust gas. This oxygen content is a quantity which is correlated to the Wobbe Index of the measured gas. However, by actually measuring or providing a quantity which represents the Wobbe Index the thermal delivery rate, i.e., BTU/minute could be obtained to control the industrial heating operation. Thus, the measuring apparatus providing such a Wobbe Index measurement would provide an efficient means of "feed forward" control to a furnace requiring a constant BTU per minute input without regard to changes in gas supply composition, density and BTU content.

SUMMARY OF THE INVENTION

An object of the present invention is to provide an improved combustible gas analyzing apparatus for determining the Wobbe Index of a combustible gas.

In accomplishing this and other objects, there has been provided, in accordance with the present invention, a combustible gas analyzing apparatus having a combustion means, a source of combustion air, a flow rate control means controlling the supply of air from the source of combustion air, pressure of a pressure regulator means for controlling the combustible gas, gas mixing means for introducing into the combustion means a combustible gas and air mixture, a detector means for detecting the oxygen content of the combustion products from the combustion means, ratio control means connected between the pressure regulator means and the mixing means for controlling the ratio of combustible gas and air supplied to the mixing means in response to a signal from the detector means to produce a preselected oxygen content of the combustion products, the ratio control means includes a variable restriction located in a flow line of the combustible gas to the mixing means and restriction monitoring means for producing a signal representative of the size of the restriction stem as an indication of the Wobbe Index of the combustible gas.

BRIEF DESCRIPTION OF THE DRAWING

A better understanding of the present invention may be had when the following detailed description is read in connection with the accompanying drawing, in which the single FIGURE is a pictorial illustration of a Wobbe Index measuring apparatus embodying an example of the present invention.

DESCRIPTION OF THE PREFERRED EMBODIMENT

Referring to the single FIGURE drawing in more detail, there is shown a measuring apparatus embodying an example of the present invention for determining the Wobbe Index of a combustible gas. An air supply (not shown) is arranged to supply air as a source of combustion oxygen through an input pipeline 2. The pipeline 2 is connected to the input of a first conventional pressure regulator 4 while the output of the pressure regulator 4 is connected to an output pipeline 6. The output pipeline 6 is connected to one input of the mixing valve 8. In a conventional fashion, the pipeline 6 is arranged to contain a fixed orifice or restriction (not shown) which is the dominating downstream restriction in the flowline supplied by the output of the pressure regulator 4. Such a fixed orifice provides a means for achieving a constant flow rate of the air from the pressure regulator 4 to form a constant flow rate air supply. Concurrently, a supply of a combustible gas (not shown) is arranged to supply a fuel gas through a second input pipeline 10 connected to the input of a second conventional pressure regulator 12. The output of the second pressure regulator 12 is supplied through an output pipeline 14 to a control valve 16. As in the case of the previously mentioned orifice in the pipeline 6, the valve 16 is arranged to provide an orifice which, while variable, in the dominating downstream restriction in the flowline supplied by the output of the second pressure regulator 12. Since a variation in the flow rate of the fuel gas is desired, a constant flow rate is only achieved for each stable setting of the valve 16 in a similar way to that provided by the orifice in the pipeline 9. The output of the control valve 16 is supplied through an output pipeline 18 to a second input of the mixing valve 8.

An output of the mixing valve 8 is supplied through pipeline 20 to a burner jet 22 for producing a combustion flame 24. The burner jet 22 and the combustion flame 24 are located within a housing 26 providing a combustion chamber for the combustion flame 24. Also located within the housing 26 would be means for initiating the burning of the combustible gas by means of a spark or other device and means for detecting the presence of the flame 24 to provide a control for the flame initiating device. Such devices are well-known in the art and, accordingly, have not been shown in the illustration of the single figure drawing. The exhaust gases from the combustion chamber 26 are allowed to escape through a restricted opening 28 in the wall of the combustion chamber 26. The aforesaid restrictions provided by the fixed restriction in the pipeline 6 and by the variable restriction of the valve 16 are each effective to provide a greater restrictive effect than that imposed by the other flowline elements, as previously mentioned, including the flow impediments imposed by the mixing connector 8, the burner 22 and the exhaust port 28. A well-known zirconium oxide detector 30 is located adjacent to the flame 24 to effect a detection of the oxygen content of the end products of the combustion process to determine a preselected combustion state, e.g., stoichiometric combustion. The output of the zirconium oxide detector 30 is applied over an output line 32 to an input of a data processing system 34 which may incorporate a microprocessor.

The valve 16 is driven by a valve motor 36 connected thereto through a valve stem 38. The valve stem 38 is connected to an apparatus for providing an indication of the position of the valve stem 38. An example of an apparatus for providing such an indication includes a lever arm 40 attached to the valve stem 38 and arranged to drive the slider 46 of a potentiometer 42 across the resistance element 44 of a potentiometer. The resistance element 44 of the potentiometer 42 is connected by electrical lines 48 and 52 to the data processor 34 while the slider 46 is connected by an electrical line 52 to the data processor 34. The data processor 34 is arranged to use the input signal from the zirconium oxide detector 30 to produce a control signal on output line 54 for controlling the operation of the valve motor 36. Concurrently, the data processor 34 may be used to produce an output signal in response to a signal from the potentiometer 42 on a data output line 56 which is connected to a recorder display 58 for displaying the position of the valve stem 38 as an indication of the Wobbe Index of the fuel gas supplied over the fuel inlet line 10.

In operation, the combustion air from the air supply controlled through the first pressure regulator 4 is supplied to the mixing valve 8 at a constant flow rate in combustion with the fuel gas supplied through the second pressure regulator 12 and the control valve 16. The combustion of the fuel gas in the presence of the air is effected by the flame 24 in the combustion chamber 26. The oxygen content of the combustion products or gases is detected by the zirconium oxide detector 30. Since the control valve 16 functions as a variable orifice, the output signal supplied to the recorder display 58 on output line 56 which is representative of the position of the valve motor 36 is a measurement of the Wobbe Index of the fuel gas. This is the result of having a short orifice, i.e., an orifice having a flow length which is less than the orifice diameter, e.g., a hole in a plate, which produces an effect dependent on the specific gravity of the fluid flowing therethrough as contrasted with a long orifice having an orifice length greater than the orifice diameter, e.g., a capillary, which produces an effect dependent on the viscosity of the fluid flowing therethrough. In the combustible gas measuring arrangement of the present invention, the variable orifice produced by the valve 16 is the only significant restriction prior to the burner 22 in the flowline containing the valve 16. In such an arrangement, the calorific, e.g., BTU, value of the gas being burned at the burner 22 will be altered if fuels of different specific gravity are introduced from the fuel line 10. In other words since:

$$H = W/\sqrt{SG}$$

then:

$$W = \frac{H}{\sqrt{SG}}$$

Accordingly, the measurement of the movement of the valve stem 38 is dependent on the square root of the specific gravity of the fuel and the calorific content and is, therefore, a direct indication of the Wobbe Index. The valve 16 is operated by the data processor 34 by means of the valve motor 36 and valve stem 38 to produce a desired combustion state, e.g., stoichiometric combustion, at the flame 24. It should be noted that stoichiometric combustion is only one point on the combustion curve which may be used and only a repeatability is necessary by returning to the same point for each measurement. The combustion level is detected by the sensor 30 as a result of the minimal amount of oxygen remaining in the combustion products from the flame 24. The representative of the Wobbe Index, i.e., valve position, may be displayed on a suitable display or recorded as a record of the Wobbe Index of the fuel gas since the recorder display 58 may include a hard copy recorder as well as a display apparatus, e.g., a cathode ray tube (CRT).

Accordingly, it may be seen that there has been provided, in accordance with the present invention, an improved gas analyzing apparatus for determining the Wobbe Index of a combustible gas.

The embodiments of the invention in which an exclusive property or priviledge is claimed are defined as follows:

1. A combustible gas analyzer comprising
 flow rate control means for supplying combustion air at a predetermined flow rate,
 pressure control means for supplying a combustible gas to be analyzed at a constant pressure,
 gas mixing means for mixing said air from said flow rate control means and a combustible gas to be analyzed,
 valve means located between said pressure control means and said mixing means for performing a valving operation on a flow of a combustible gas to be analyzed to said mixing means, said valve means including a variable restriction and drive means for varying said restriction,
 combustion means connected to an output of said mixing means for producing a combustion of a mixture of said air and said combustible gas from said mixing means, detector means for detecting the oxygen content of combustion products from the combustion of said air and said combustible gas by said combustion means, control means responsive to said detector means for producing a control signal for controlling said valving operation of said valve means to achieve a preselected oxygen content of said combustion products, circuit means for applying said control signal to said drive means to effect a corresponding variation of said variable restriction, monitoring means for monitoring the size of said restriction to produce a signal representative of the size of said restriction and display means for displaying said signal from said monitoring means as an indication of the Wobbe Index of said combustible gas.

2. A combustible gas analyzer as set forth in claim 1 wherein said preselected oxygen content of said combustion products is representative of substantially stoichiometric combustion.

3. A combustible gas analyzer as set forth in claim 1 wherein said variable restriction includes a selectively variable orifice and said drive means includes a valve stem arranged to vary said orifice by a corresponding movement of said stem and a valve stem drive motor, said circuit means applying said control signal to said drive motor and said monitoring means being arranged to produce said signal representative of the position of said valve stem produced by said movement.

4. A combustible gas analyzer as set forth in claim 3 wherein valve stem movement monitoring means includes a potentiometer having a resistance element and a contact slider in contact with said resistance element and connected to said valve stem to be driven across said resistance element by said valve stem.

5. A combustible gas analyzer as set forth in claim 1 wherein said combustion means includes a gas burner connected to an output of said gas mixing means, a combustion chamber surrounding said gas burner to a gas-tight enclosure and a combustion product exhaust for providing a restricted gas exhaust from said combustion chamber.

6. A combustible gas analyzer as set forth in claim 5 wherein said detector means includes a zirconium oxide detector positioned within said combustion chamber adjacent to said gas burner to sense the oxygen content of said combustion products.

7. A method for analyzing a combustible gas to determine the Wobbe Index of the gas including the steps of supplying air as a source of combustion oxygen at a constant flow rate and a combustible gas to be analyzed at a constant pressure, passing the gas through a valve arranged to provide a variable restriction to the flow of the gas, mixing the air and the gas output of the valve, producing a combustion of the mixed gas and air, detecting the oxygen content of the combustion products resulting from the combustion of the gas and air, controlling the valve restriction to provide a preselected oxygen content of the combustion products and monitoring the size of the restriction imposed by the valve as an indication of the Wobbe Index of the gas to be analyzed.

8. A method as set forth in claim 7 wherein said preselected oxygen content is representative of substantially stoichiometric combustion of the combustible gas.

9. A method as set forth in claim 7 wherein the valve includes a valve stem and a valve stem drive means for varying the size of the variable restriction by a movement of the valve stem and the controlling of the valve includes the step of energizing the valve stem drive means to vary the size of the variable restriction while the step of monitoring the size of the valve restriction includes the step of monitoring the position of the valve stem.

10. A method as set forth in claim 9 wherein the step of monitoring the position of the valve stem includes the step of connecting the valve stem to a slider on a potentiometer and measuring the voltage sensed by the slider as an indication of the position of the valve stem.

* * * * *